(12) United States Patent
Liu et al.

(10) Patent No.: US 9,943,622 B2
(45) Date of Patent: Apr. 17, 2018

(54) MINIMIZING BIOLOGICAL LIPID DEPOSITS ON CONTACT LENSES

(71) Applicant: Bausch & Lomb Incorporated, Rochester, NY (US)

(72) Inventors: X. Michael Liu, Pittsford, NY (US); Joseph A. Chinn, Lafayette, CO (US); George L. Grobe, III, Ontario, NY (US); E. Peter Maziarz, Brockport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 60 days.

(21) Appl. No.: 14/427,928

(22) PCT Filed: Sep. 24, 2013

(86) PCT No.: PCT/US2013/061416
§ 371 (c)(1),
(2) Date: Mar. 12, 2015

(87) PCT Pub. No.: WO2014/058613
PCT Pub. Date: Apr. 17, 2014

(65) Prior Publication Data
US 2016/0022860 A1    Jan. 28, 2016

Related U.S. Application Data

(60) Provisional application No. 61/710,980, filed on Oct. 8, 2012.

(51) Int. Cl.
| | |
|---|---|
| *A61L 12/14* | (2006.01) |
| *C11D 1/62* | (2006.01) |
| *C11D 3/00* | (2006.01) |
| *C11D 3/48* | (2006.01) |
| *A61K 9/00* | (2006.01) |

(52) U.S. Cl.
CPC ............ *A61L 12/143* (2013.01); *A61L 12/14* (2013.01); *A61L 12/145* (2013.01); *C11D 1/62* (2013.01); *C11D 3/0078* (2013.01); *C11D 3/48* (2013.01); *A61K 9/0051* (2013.01)

(58) Field of Classification Search
None
See application file for complete search history.

(56) References Cited

U.S. PATENT DOCUMENTS

| | | |
|---|---|---|
| 4,758,595 A | 7/1988 | Ogunbiyi et al. |
| 4,786,436 A | 11/1988 | Ogunbiyi et al. |
| 5,300,296 A | 4/1994 | Holly et al. |
| 5,604,189 A | 2/1997 | Zhang et al. |
| 5,631,005 A | 5/1997 | Dassanayake et al. |
| 5,765,579 A | 6/1998 | Heiler et al. |
| 5,773,396 A | 6/1998 | Zhang et al. |
| 7,025,958 B2 | 4/2006 | Schlitzer et al. |
| 8,119,112 B2 | 2/2012 | Xia et al. |
| 2008/0096966 A1 | 4/2008 | Burke et al. |
| 2010/0086514 A1* | 4/2010 | Liu .......................... A01N 33/12 424/78.08 |
| 2010/0178317 A1* | 7/2010 | Burke ..................... A01N 25/30 424/429 |
| 2011/0263717 A1 | 10/2011 | Fridman |

FOREIGN PATENT DOCUMENTS

| | | |
|---|---|---|
| CN | 1125463 A | 6/1996 |
| CN | 1279710 A | 1/2001 |
| JP | 2002322048 A | 11/2002 |
| KR | 1020100121474 | 11/2010 |
| WO | 95/00617 A1 | 1/1995 |
| WO | 99/27060 A1 | 6/1999 |
| WO | 01/57172 A1 | 8/2001 |
| WO | 2009097028 | 8/2009 |

OTHER PUBLICATIONS

Korean Intellectual Patent Office (KIPO) Preliminary Rejection Apr. 20, 2016 (English translation provided by Kim & Chang Intellectual Property.
Chinese Office Action dated Jun. 7, 2016 and translation provided by Marks & Clerk China (22 pages).
Guidance for Industry-Premarket Notification (510(k)) Guidance Document for Contact Lens Care Products (May 5, 1997)—U.S. Food and Drug Administration (pp. 97-98).
PCT International Preliminary Report on Patentability in corresponding International Application No. PCT/US2013/061416 dated Feb. 2, 2015.
Lu et al.: Hydroxypropyl guar-borate interactions with tear film mucin and lysozyme. Website: http://www.ncbi.nlm.nih.gov/pubmed/?term=hydroxypropyl+guar-borate . . . Printed Sep. 10, 2013.
Galactasol™ hydroxypropyl guar Website: http://www.ashland.com/products/galactasol-hydroxypropyl-guar. Printed May 7, 2012.
Galactasol™ carboxymethyl hydroxypropyl guar Website: http://www.ashland.com/products/galactasol-carboxymethyl-hydroxypropyl-guar. Printed May 7, 2012.
Guar Derivatives—Hydroxypropyl Guar, Carboxymethyl Guar, Carboxymethyl Hydroxyp . . . Website: http://www.encorenaturalpolymers.com/product_oil_gas_well_drilling_fracturing.htm Printed May 7, 2012.

(Continued)

*Primary Examiner* — Susan Tran
(74) *Attorney, Agent, or Firm* — Andrew J. Anderson, Esq.; Harter Secrest & Emery LLP

(57) ABSTRACT

Method for minimizing the sorption of tear lipids on frequent replacement, or extended-wear, contact lenses, the method comprising (a) contacting the contact lens selected from the group consisting of senofilcon A, lotrafilcon A, lotrafilcon B, and comfilcon A B with a lens care solution for a period of at least three hours to minimize the accumulation of tear lipids on the contact lens. The lens care solution comprises 0.5 ppm to 10 ppm α-[4-tris(2-hydroxyethyl)-ammonium chloride-2-butenyl]poly[1-dimethyl ammonium chloride-2-butenyl]-ω-tris(2-hydroxyethyl) ammonium chloride; citrate, citric acid or a mixture thereof; and 0.005 wt. % to 0.05 wt. % hyaluronic acid. The method also includes (b) inserting the soaked contact lens into one's eye, and (c) repeating steps (a) and (b).

7 Claims, No Drawings

(56) References Cited

OTHER PUBLICATIONS

Guar Gum: Overview Website: http://www.guargum.biz/guargum_chemical_structure.html Printed Sep. 10, 2013.
Pitt et al.: Quantitation of cholesterol and phospholipid sorption on silicone hydrogel contact lenses © 2013 Wiley Periodicals, Inc. (Nov. 8, 2012).

* cited by examiner

MINIMIZING BIOLOGICAL LIPID DEPOSITS ON CONTACT LENSES

FIELD OF THE INVENTION

This invention relates to lens care compositions and, in particular, to a method for minimizing biological lipid deposits on extended-wear or frequent replacement contact lenses.

BACKGROUND

Contact lenses in wide use today fall into two categories. First, there are the hard or rigid corneal type lenses that are formed from materials prepared by the polymerization of acrylic esters, such as polymethylmethacrylate (PMMA). Second, there are the hydrogel or soft type of lenses made by polymerizing hydrophilic monomers such as 2-vinyl pyrrolidone, 2-hydroxyethyl methacrylate (HEMA), or in the case of extended wear, silicone hydrogel contact lenses, by polymerizing silicon-containing monomers or macromonomers with one or more hydrophilic monomers. Solutions that wet the lenses before insertion in the eye are required for both the hard and soft types of contact lenses. After the contact lenses are inserted in the eye, ophthalmic solutions for rewetting, lubricating, and/or enhancing patient comfort (e.g., less dryness, or less end of day irritation) are sometimes applied to the eye by means of a drop dispenser.

Those skilled in the art have long recognized that surface characteristics play a major role in biocompatibility, and more importantly, with a patient's sense of comfort with wearing contact lenses throughout the day and evening. The ionic surface of soft contact lenses can interact with biological components of the tear film, which includes several different ocular proteins, lipids, mucins, and enzymes. The sorption (absorption and adsorption) of tear lipids onto the surface of a contact lens is a common problem and the extent of lipid sorption will depend upon a number of factors including the nature of the lens material from which the lens is made. The accumulation of tear lipids on a lens surface, particularly with frequent replacement lenses (FRPs) or extended-wear lenses (EWs), can lead to dehydration, non-wettability or poor visual quality of the lens and promote tear film instability resulting in patient discomfort.

It is now accepted that increasing the hydrophilicity of the contact lens surface improves the wettability of the contact lenses, which in turn is often associated with improved comfort with wearing contact lenses throughout the day. As stated, the surface of the lens can affect the lens's susceptibility to sorption or accumulation of lipids naturally present in tear fluid. Extended-wear lenses, i.e. lenses used without daily removal of the lens before sleep, present additional challenges. Lipid accumulation can become a significant problem as the lenses must possess a high level comfort and biocompatibility during the time they remain in the eye—in many instance from 7 to 30 days.

Rewetting solutions can improve the comfort of wearing soft contact lenses during the day by increasing the surface wettability, and are added directly to the contact lens in the eye. Such solutions typically contain viscosity enhancing agents, lubricants, surfactants, buffers, preservatives, and salts. For example, U.S. Pat. No. 4,786,436 to Ogunbiyi, et al. describes contact lens wetting solutions that can include collagen and other demulcents such as hydroxylethyl cellulose, methyl cellulose, carboxymethyl cellulose, hydroxypropyl methylcellulose, hydroxylpropyl-cellulose and the like.

PCT Application (Publication No. WO 01/057172) describes a contact lens care solution that includes a polysaccharide with a molecular weight of 5000 daltons or greater (0.005 to 10 wt. %), a nonionic surfactant (0.01 to 10 wt. %) and a polymeric preservative (0.00001 to 1 wt. %). An exemplary solution is provided as Example No. 5. This solution includes 0.02 wt. % sodium hyaluronate, 1.0 wt. % poloxamine (Tetronics®1107), 0.125 wt. % $Na_2EDTA$ and 1 ppm of PHMB in a phosphate buffer. U.S. Pat. No. 5,765,579 to Heiler et al. describes lens care compositions to clean and disinfect contact lenses. The compositions include a sulfobetaine compound to help remove protein deposits from the surface of contact lenses. A preferred sulfobetaine is sulfobetaine 3-10. Lastly, U.S. Pat. Nos. 5,604,189 and 5,773,396 to Zhang et al. describe a composition for cleaning and wetting contact lenses comprising (i) a non-amine polyethyleneoxy-containing compound having an HLB of at least about 18, (ii) a surface active agent having cleaning activity for contact lens deposits that may have an HLB less than 18, and (iii) a wetting agent.

It would, therefore, be desirable to develop a contact lens care solution that could be used to periodically clean and disinfect contact lenses upon removal of the lens from the eye, or a solution applied directly to the eye as in a rewetting solution, that would minimize the sorption of lipids on the lens surface.

SUMMARY OF THE INVENTION

A method for minimizing the sorption of tear lipids on frequent replacement, or extended-wear, contact lenses, the method comprising (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises 0.5 ppm to 10 ppm α-[4-tris(2-hydroxyethyl)-ammonium chloride-2-butenyl]poly[1-dimethyl ammonium chloride-2-butenyl]-ω-tris(2-hydroxyethyl) ammonium chloride; citrate, citric acid or a mixture thereof; and 0.005 wt. % to 0.05 wt. % hyaluronic acid. The method also includes (b) inserting the soaked contact lens into one's eye, and (c) repeating steps (a) and (b).

A method for minimizing the sorption of tear lipids on frequent replacement, or extended-wear, contact lenses, the method comprising (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises 0.5 ppm to 10 ppm α-[4-tris(2-hydroxyethyl)-ammonium chloride-2-butenyl]poly[1-dimethyl ammonium chloride-2-butenyl]-ω-tris(2-hydroxyethyl) ammonium chloride; citrate, citric acid or a mixture thereof; and 0.01 wt. % to 0.8 wt. % of an amphoteric surfactant of general formula I

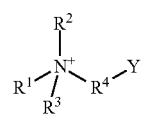

I wherein $R^1$ is R or $—(CH_2)_n—NHC(O)R$, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$. The method also includes (b) inserting the soaked contact lens into one's eye, and (c) repeating steps (a) and (b).

A method for minimizing the sorption of tear lipids on frequent replacement, or extended-wear, contact lenses, the method comprising (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises 0.5 ppm to 10 ppm α-[4-tris(2-hydroxyethyl)-ammonium chloride-2-butenyl]poly[1-dimethyl ammonium chloride-2-butenyl]-ω-tris(2-hydroxyethyl) ammonium chloride; citrate, citric acid or a mixture thereof; and 0.02 wt. % to 0.1 wt. % of a neutral, methyl cellulose, the methyl cellulose having a weight average molecular weight from 80 kDa to 250 kDa. The method also includes (b) inserting the soaked contact lens into one's eye, and (c) repeating steps (a) and (b).

The lens care solutions must also satisfy the Stand-Alone Procedure for Disinfecting Products based on the Disinfection Efficacy Testing for Products dated May 1, 1997 of the U.S. Food and Drug Administration, Division of Ophthalmic Devices, which requires the solution to pass primary criteria over a minimum recommended disinfection period in that that the number of bacteria recovered per mL must be reduced by a mean value of not less than 3.5 logs, and the number of mold and yeast recovered per ml must be reduced by a mean value of not less than 1.5 log within the disinfection period.

DETAILED DESCRIPTION OF THE INVENTION

Daily disposable contact lenses are designed to be worn just once; they are thrown out at the end of each day and new contacts are put in the following day. These contact lenses are ideal for those who lack the patience, time, and/or discipline to clean and disinfect lenses. Frequent replacement contact lenses are designed to be worn each day then taken out, cleaned, and stored before bedtime. The replacement frequency for these contact lenses can range from weekly to monthly, or even bi-monthly, and varies largely among individuals. On an annual basis, these contacts are slightly less costly than daily disposable lenses and are currently the most widely used disposable contact lenses today. Extended wear contact lenses are designed to be worn for 30 days straight. The concept of extended wear contact lenses has been around for a long time, but only recently has technology improved enough to make them a reality. These contact lenses are ideal for those patients who would prefer to put contacts in and then forget about them for a month. Also, many patients who wear extended wear lenses choose to remove them each night or very other night for cleaning, i.e., the care regimen is no different than that of frequent replacement lenses.

The present invention addresses the concerns of patients who wear frequent replacement, and for those patients who wear extended wear contact lenses and remove them for periodic cleaning and disinfection. Yet, in spite of the cleaning regimens used, many of these patients experience an increase in discomfort as the contact lens nears the end of its stated wear period, whether that is 14 or 30 days. This discomfort is often attributed to the build-up of biological tear lipids and denatured tear proteins on both the anterior and posterior surface of the contact lens. Moreover, to reduce the financial costs of contact lenses some patients will over-extend the wear time of their lenses. While this practice is frowned upon by both the contact lens manufacturer and eye care professional, and efforts are made to educate patients against such practices, some patients continue to extend their lenses as well as their dollars through this practice. The result is that some patients will experience discomfort as the lens approaches the end of its wear life.

The lens care compositions described herein are developed to minimize the interaction of tear lipids with a surface of contact lens, and therefore, minimize the accumulation of tear lipids over the wear-life of the lens. In this manner, the lens care solutions described herein minimize the accumulation of tear lipids over time, particularly, over 14 to 28 days of wear with periodic removal and cleaning of the lenses. The invention is directed to a method for minimizing the sorption of tear lipids on frequent replacement, or extended-wear, contact lenses.

The term "sorption" means the taking up and holding of one substance by another. Sorption includes the processes of adsorption and absorption. Adsorption is the adhesion or attachment of molecules of a compound, e.g., cholesterol or other ocular lipids, to a surface of a material, e.g., the surface of a contact lens. Absorption is the adhesion or attachment of molecules within a material.

Of course, it is to be understood by a person of ordinary skill that the more times a patient removes an FRP or EW lens for cleaning and disinfecting, the more likely the lens will have less accumulated tear lipid on the surface of a lens during the wear-life of the lens. Accordingly, it is recommended that a patient remove a FRP lens or an EW lens on daily basis for cleaning and disinfection. It is common, however, for contact lens patients to skip one or two days, before removing their lenses for cleaning and disinfection. To minimize the accumulation of tear lipids on a surface of a FRP lens or an EW lens, it is recommended that a patient remove their lenses for cleaning at least once every seven days, or at least twice in a 14-day period.

In one embodiment, the method includes: (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises: 0.5 ppm to 10 ppm α-[4-tris(2-hydroxyethyl)-ammonium chloride-2-butenyl] poly[1-dimethyl ammonium chloride-2-butenyl]-ω-tris(2-hydroxyethyl) ammonium chloride (polyquaternium-1); citrate, citric acid or a mixture thereof; and 0.005 wt. % to 0.05 wt. % hyaluronic acid. Following the contacting period, the lens is removed from a lens holding case and (b) inserted into the patient's eye. The patient then repeats steps (a) and (b).

In another embodiment, the method includes: (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises: 0.5 ppm to 10 ppm α-[4-tris(2-hydroxyethyl)-ammonium chloride-2-butenyl] poly[1-dimethyl ammonium chloride-2-butenyl]-ω-tris(2-hydroxyethyl) ammonium chloride (polyquaternium-1); citrate, citric acid or a mixture thereof; and 0.01 wt. % to 0.8 wt. % of an amphoteric surfactant of general formula I

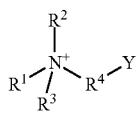

wherein $R^1$ is R or —$(CH_2)_n$—NHC(O)R, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$. Following the contacting period, the lens is removed from a lens holding case and (b) inserted into the patient's eye. The patient then repeats steps (a) and (b).

In yet another embodiment, the method includes: (a) contacting the contact lens selected from the group consisting of senofilcon A, lotrafilcon A, lotrafilcon B, and comfilcon A with a lens care solution for a period of at least three hours to minimize the accumulation of tear lipids on the contact lens. The lens care solution comprises: 0.5 ppm to 10 ppm α-[4-tris(2-hydroxyethyl)-ammonium chloride-2-butenyl]poly[1-dimethyl ammonium chloride-2-butenyl]-ω-tris (2-hydroxyethyl) ammonium chloride (polyquaternium-1); citrate, citric acid or a mixture thereof; and 0.02 wt. % to 0.1 wt. % of a neutral, methyl cellulose, the methyl cellulose having a weight average molecular weight from 80 kDa to 250 kDa. Following the contacting period, the lens is removed from a lens holding case and (b) inserted into the patient's eye. The patient then repeats steps (a) and (b).

With respect to each of the above three embodiments, the lens care solution must also satisfy the Stand-Alone Procedure for Disinfecting Products based on the Disinfection Efficacy Testing for Products dated May 1, 1997 of the U.S. Food and Drug Administration, Division of Ophthalmic Devices, which requires the solution to pass primary criteria over a minimum recommended disinfection period in that that the number of bacteria recovered per mL must be reduced by a mean value of not less than 3.5 logs, and the number of mold and yeast recovered per ml must be reduced by a mean value of not less than 1.5 log within the disinfection period.

The amphoteric surfactants of general formula I are surface-active compounds with both acidic and alkaline properties. The amphoteric surfactants of general formula I include a class of compounds known as betaines. The betaines are characterized by a fully quaternized nitrogen atom and do not exhibit anionic properties in alkaline solutions, which means that betaines are present only as zwitterions at near neutral pH.

All betaines are characterized by a fully quaternized nitrogen. In alkyl betaines, one of the alkyl groups of the quaternized nitrogen is an alkyl chain with eight to sixteen carbon atoms. One class of betaines is the sulfobetaines or hydroxysulfobetaines in which the carboxylic group of alkyl betaine is replaced by sulfonate. In hydroxysulfobetaines a hydroxy-group is positioned on one of the alkylene carbons that extend from the quaternized nitrogen to the sulfonate. In alkylamido betaines, an amide group is inserted as a link between the hydrophobic $C_8$-$C_{16}$alkyl chain and the quaternized nitrogen.

Accordingly, the invention is directed to ophthalmic compositions comprising: 0.5 ppm to 10 ppm of a cationic antimicrobial component selected from the group consisting of biguanides, polymeric biguanides, quaternium ammonium compounds and any one mixture thereof; 0.005 wt. % to 0.15 wt. % of hyaluronic acid; and 0.01 wt. % to 1.0 wt. % of an amphoteric surfactant of general formula I

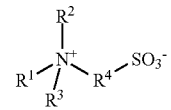

wherein $R^1$ is R or —$(CH_2)_n$—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$alkylene optionally substituted with hydroxyl.

In one embodiment, the hyaluronic acid is present from 0.002 wt. % to 0.04 wt. %, and the cationic, antimicrobial component is poly(hexamethylene biguanide). Accordingly, one of the more preferred compositions comprises 0.5 ppm to 3.0 ppm of poly(hexamethylene biguanide); 0.002 wt. % to 0.04 wt. % hyaluronic acid; and 0.01 wt. % to 1 wt. % of an amphoteric surfactant of general formula I.

Certain sulfobetaines of general formula I are more preferred than others. For example, Zwitergent®3-10 available from Calbiochem Company, is a sulfobetaine of general formula I wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding Zwitergent®3-08 ($R^1$ is a is a straight, saturated alkyl with eight carbons), Zwitergent®3-12 ($R^1$ is a is a straight, saturated alkyl with twelve carbons), Zwitergent®3-14 ($R^1$ is a is a straight, saturated alkyl with fourteen carbons) and Zwitergent®3-16 ($R^1$ is a is a straight, saturated alkyl with sixteen carbons). Accordingly, some of the more preferred ophthalmic composition will include a sulfobetaine of general formula II wherein $R^1$ is a $C_8$-$C_{16}$alkyl and $R^2$ and $R^3$ is methyl.

In another embodiment, the amphoteric surfactant of general formula I is a hydroxysulfobetaine of general formula II

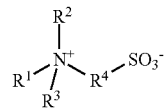

wherein $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

In another embodiment, the amphoteric surfactant is an alkylamido betaine of general formula III

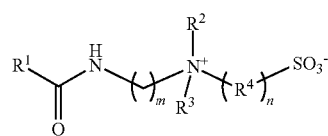

wherein $R^1$ is a $C_8$-$C_{16}$alkyl, and m and n are independently selected from 2, 3, 4 or 5; $R^2$ and $R^3$ are each independently selected from a $C_1$-$C_4$alkyl optionally substituted with hydroxyl; and $R^4$ is a $C_2$-$C_8$alkylene optionally substituted with hydroxyl. The most common alkylamido betaines are alkylamidopropyl betaines, e.g., cocoamidopropyl dimethyl betaine and lauroyl amidopropyl dimethyl betaine.

Hyaluronic acid is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

Methyl cellulose is a chemical compound derived from cellulose. It is a hydrophilic white powder in pure form and dissolves in cold (but not in hot) water, forming a clear viscous solution or gel. It is sold under a variety of trade names and is used as a thickener and emulsifier in various food and cosmetic products, Contact Lens Care Solutions As indicated above, the lens care solution will also include the antimicrobial component, α-[4-tris(2-hydroxyethyl)-ammonium chloride-2-butenyl]poly[1-dimethyl ammonium chloride-2-butenyl]-ω-tris(2-hydroxyethyl) ammonium chloride, also referred to in the art as polyquaternium-1. Polyquaternium-1 is present in a contact lens care solution from 0.5 ppm to 10 ppm. In some embodiments, the lens care solution can include other known antimicrobial components including other quaternary ammonium compounds (including small molecules) and polymers and low and high molecular weight biguanides. Polyquaternium-42 is one of the more preferred polyquaternium compounds, see, U.S. Pat. No. 5,300,296. Polyquaternium-42 is present in the ophthalmic compositions from 5 ppm to 50 ppm. The biguanides include the free bases or salts of alexidine, chlorhexidine, hexamethylene biguanides and their polymers, and combinations thereof. The salts of alexidine and chlorhexidine can be either organic or inorganic and include gluconates, nitrates, acetates, phosphates, sulfates, halides and the like.

In those solutions in which the polyquaterium-1 is supplemented with another antimicrobial component, one preferred antimicrobial component of choice is a polymeric biguanide known as poly(hexamethylene biguanide) (PHMB or PAPB) commercially available from Arch Chemical under the trademark Cosmocil™ CQ. The PHMB is present in the compositions from 0.2 ppm to 5 ppm or from 0.5 ppm to 2 ppm. In another preferred embodiment, the polyquaternium-1 is supplemented with 1,1'-hexamethylene-bis[5-(2-ethylhexyl)biguanide], which is referred to in the art as "alexidine". The alexidine is present in the compositions from 0.5 ppm to 5 ppm or from 0.5 ppm to 2 ppm.

It is well known that polyquaternium-1 has relatively low antimicrobial activity against select fungal species, particularly, C. albicans and F. solani. To supplement the polyquaternium-1 against the fungal strains, one can include any one of the above antimicrobial components or an amido amine. One such amido amine is N,N-dimethyl-N'-dodecanoyl-1,3-propylenediamine, also referred to in the art as Aldox®. See, U.S. Pat. Nos. 5,631,005 and 7,025,958.

It is to be understood by those in the art that the compositions can include one or more of the antimicrobial components described above. For example, in one embodiment, the ophthalmic compositions include polyquaternium-1 in combination with a biguanide antimicrobial component such as poly(hexamethylene biguanide). The polyquaternium-1 is present in relatively low concentrations, that is, from 0.5 ppm to 3 ppm, relative to the reported concentration of polyquaternium-1 in both Opti-Free®Express and Opti-Free®Replenish. Applicants believe that the polyquaternium-1 and the PHMB, in combination, may enhance the biocidal efficacy of the ophthalmic compositions.

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include an effective amount of a surfactant component, in addition to the amphoteric surfactant of general formula I, a viscosity inducing or thickening component, a chelating or sequestering component, or a tonicity component. The additional component or components can be selected from materials which are known to be useful in contact lens care solutions and are included in amounts effective to provide the desired functional characteristic.

Suitable surfactants can be cationic or nonionic, and are typically present (individually or in combination) in amounts up to 2% w/v. One preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred surfactant is tyloxapol.

A particular non-ionic surfactant consisting of a poly (oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The foregoing poly (oxyethylene) poly(oxypropylene) block polymer surfactants will generally be present in a total amount from 0.0 to 2% w/v, from 0. to 1% w/v, or from 0.2 to 0.8% w/v An analogous of series of surfactants, for use in the lens care compositions, is the poloxamer series which is a poly(oxyethylene) poly(oxypropylene) block polymers available under Pluronic® (commercially available from BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

The present invention is directed in certain embodiments to ophthalmic compositions comprising an ethyleneoxide-butyleneoxide (EO—BO) block copolymer of the formula $(EO)_m(BO)_n$ where m is an integer having an average value of 10 to 1000 and n is an integer having an average value of 5 to 1000. It is believed that the ethyleneoxide butyleneoxide block copolymers interact with hyaluronic acid in the aqueous lens care compositions. Aqueous compositions comprising EO—BO copolymers are generally Newtonian in behavior, and EO—BO copolymer contributes little to the viscosity of such composition at the relatively low concentrations present in such concentrations. However, the hyaluronic acid and EO—BO copolymers have a synergistic increase in viscosity relative to compositions comprising hyaluronic acid or EO—BO alone. Compositions with hyaluronic acid and EO—BO compositions have desirable viscoelastic and interfacial properties that make them well suited for contact lens care applications such as for disinfection and rewetting of contact lenses.

EO—BO block copolymers are somewhat more hydrophobic in aqueous solutions than the corresponding ethyleneoxide-propyleneoxide copolymers sold under the trademark Pluronics® and Tetronics®. The preferred copolymers of formula $(EO)_m(BO)_n$ are those wherein there is a predominance of EO to BO segments. That is, the variable "m" in the above formula is preferably greater than the variable "n". The EO—BO block copolymers will preferably have a ratio of EO to BO segments of from about 2:1 to about 10:1, with a ratio of about 3:1 to about 6:1 being most preferred. At an air-water interface these nonionic surfactants form elastic layers that can provide a cushioning effect for contact lenses when used in ophthalmic solutions. In a preferred embodiment, the compositions described herein include an EO—BO block copolymer and hyaluronic acid. Some ophthalmic applications of such compositions include contact lens disinfection solutions, dry eye and artificial tear compositions. The EO—BO copolymer can be present at a concentration of 0.001 wt. % to 0.6% wt. %, or from 0.05 wt. % to 0.2% wt. %.

The solutions employed in the present invention can be prepared by a variety of techniques. One method employs two-phase compounding procedures. In the first phase, about 30 percent of the distilled water is used to dissolve the cationic cellulosic polymer by mixing for about 30 minutes at around 50° C. The first-phase solution is then autoclaved at about 120° C. for 30 minutes. In a second phase, alkali metal chlorides, sequestering agents, preservatives and buffering agents are then dissolved in about 60 percent of the distilled water under agitation, followed by the balance of distilled water. The second-phase solution can then be sterilely added into the first-phase solution by forcing it through an 0.22 micron filter by means of pressure, followed by packaging in sterilized plastic containers.

As indicated above, the present invention is useful for improving comfort and wearability for extended-wear contact lenses. For that purpose, compositions for use in the present invention may be formulated as eye-drops and sold in a wide range of small-volume containers from 1 to 30 ml in size. Such containers can be made from HDPE (high density polyethylene), LDPE (low density polyethylene), polypropylene, poly(ethylene terephthalate) and the like. Flexible bottles having conventional eye-drop dispensing tops are especially suitable for use with the present invention. The eye-drop formulation of the invention used by instilling, for example, about one (1) or three (3) drops in the eye(s) as needed.

The present invention is also useful as a component of a cleaning, disinfecting or conditioning solution. The invention may also include antimicrobial agents, surfactants, toxicity adjusting agents, buffers and the like that are known to be useful components of conditioning and/or cleaning solutions for contact lenses. Examples of suitable formulations for cleaning and/or disinfecting solutions are taught in U.S. Pat. No. 5,858,937 to Richard and Heiler, which is incorporated by reference as if set forth at length herein.

Examples

Three solution components, methylcellulose (MC, low or high molecular weight form), sulfobetaine 3-10 (SB3-10) and hyaluronic acid (HA, 1.2-1.4 MDa), were added to a commercially available multipurpose lens care solution, PureMoist® from Alcon, Inc. The purpose of the study is to determine the effect each of the solution components would have on preventing the sorption of cholesterol on Acuvue Oasys® contact lenses from Johnson & Johnson. Cholesterol is one component of a simulated lipid-tear solution, the components of which and their respective concentrations are provided in the table below. The contact lenses are removed from commercially sealed packaging, rinsed with then soaked overnight in borate buffered saline (BBS), 5 mL, to remove components present in the lens packaging solution. Three lenses are used per study trial, and the amount of cholesterol sorbed on the lenses and reported in Table 2 is the average of the three trials. The lens is removed from the BBS and soaked in Example Solutions 1 to 6 for 16 hours at 35° C. (see Table 2). The lens is removed and blot dried with a Kimwipe®. The lens is placed in a small vial with 1×3 mL of 50/50 methanol/chloroform solution to remove any sorbed lipids and cholesterol for 4 hours. The concentration of cholesterol in the extraction solution was then determined using high performance liquid chromatography with an evaporative light scattering detector (HPLC-ELSD). BBS, BBS with 0.05 wt % MC (HMW), and PureMoist® are used as control solutions and the cholesterol sorption date is listed in Table 1. The low molecular weight from of MC has a weight average molecular weight of 48,000 Da as determined by GPC. The high molecular weight from of MC has a weight average molecular weight of 148,000 Da.

Simulated Lipid-Tear Solution

| tear solution | mg [a] |
|---|---|
| cholesterol | 16 |
| dextrin | 40 |
| DPPC [b] | 35 |
| lysozyme | 13.4 |
| lactoferrin | 17.9 |
| albumin | 43.5 |
| mucin | 50 |

[a] in 500 mL of BBS
[b] DPPC is dipalmitoylphosphatidylcholine

The simulated lipid-tear solution is prepared by adding the tear solution components in the listed amounts to 500 mL of BBS. Initially, the lipid-tear solution is slightly cloudy, but following gentle stirring overnight at 35° C. the solution turns clear.

HPLC-ELSD Analytical Test Procedure

An Agilent 100 HPLC with a ChemStation data interface and equipped with a Astec Diol, 250×4.6 mm column is used to determine the total amount of cholesterol in micrograms that is extracted from a contact lens. The mobile phase solution is 71 wt % chloroform, 26 wt % methanol and 3 wt % 10 mM ammonium nitrate. The flow rate is 1.0 mL/min, column temperature is 40° C., and an injection volume of 50 μL is used. A Alltech ELSD 800 is used to detect the cholesterol with a drift tube temperature of 110° C., gas pressure of 2.9 bar and an output range of 10 mV.

TABLE 1

Control Solution Data

| control solution | μg/lens |
|---|---|
| BBS | 37.5 |
| BBS + 0.05 MC (HMW) | 16.5 [a] |
| PureMoist® | 40.9 |

[a] represents a 56% reduction in cholesterol sorption

TABLE 2

Percent cholesterol reduction from PureMoist® control

| Example | μg/lens | reduction |
|---|---|---|
| No. 1, PureMoist® + 0.005% MC (HMW) | 34.5 | 16% |
| No. 2, PureMoist® + 0.005% MC (LMW) | 34.6 | 15% |
| No. 3, PureMoist® + 0.05% MC (HMW) | 37.5 | 8% |
| No. 4, PureMoist® + 0.05% MC (LMW) | 24.8 | 39% |
| No. 5, PureMoist® + 0.1% SB3-10 | 21.1 | 48% |
| No. 6, PureMoist® + 0.02% HA | 14.4 | 65% |

The cholesterol sorption control data of Table 1 is interesting in itself because it indicates that PureMoist® MPS is no better than BBS in minimizing the sorption of the lipid, cholesterol, using the overnight soak procedure outlined above.

The cholesterol sorption control data of Table 2 indicates that the addition of methyl cellulose (MC) (HMW) at a concentration of 0.005 wt % or 0.05 wt % to PureMoist® is only slightly effective at minimizing the sorption of the cholesterol. A similar poor result is observed for MC (LMW) at a concentration of 0.005 wt % in PureMoist®, however, there is significant improvement in minimizing cholesterol if the concentration of MC (LMW) is increased to 0.05 wt %. The addition of 0.1 wt % sulfobetaine 3-10 (SB3-10), or 0.02 wt % hyaluronic acid (HA), to PureMoist® exhibits exceptional lipid prevention (cholesterol sorption) results. As indicated, SB3-10 reduces cholesterol sorption by 48% (cuts cholesterol sorption by half vs. PureMoist® control), and HA reduces cholesterol sorption by 65% (cuts cholesterol sorption by more than half vs. PureMoist® control).

We claim:

1. A method for minimizing the sorption of tear lipids on frequent replacement, or extended-wear, contact lenses, the method comprising:
 (a) contacting the contact lens selected from the group consisting of senofilcon A, lotrafilcon A, lotrafilcon B, and comfilcon A with a lens care solution for a period of at least three hours to minimize the accumulation of tear lipids on the contact lens, the lens care solution comprising:
 0.5 ppm to 10 ppm α-[4-tris(2-hydroxyethyl)-ammonium chloride-2-butenyl]poly[1-dimethyl ammonium chloride-2-butenyl]-ω-tris(2-hydroxyethyl) ammonium chloride;

citrate, citric acid or a mixture thereof; and
a lipid sorption inhibitor selected from the group consisting of:
  hyaluronic acid at a concentration of 0.005 wt. % to 0.05 wt. %; and
  an amphoteric surfactant of general formula I at a concentration of 0.01 wt. % to 0.8 wt. %

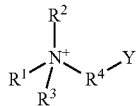

I wherein $R^1$ is R or —$(CH_2)$n-NHC(O)R, wherein R is a $C_8$-$C_{30}$ alkyl optionally substituted with hydroxyl and n is 2, 3 or 4; $R^2$ and $R^3$ are each independently selected from the group consisting of hydrogen and $C_1$-$C_4$ alkyl; $R^4$ is a $C_2$-$C_8$ alkylene optionally substituted with hydroxyl; and Y is $CO_2$ or $SO_3$; and
(b) inserting the contacted contact lens into one's eye; and
(c) repeating steps (a) and (b);
wherein the lens care solution meets the Stand-Alone Procedure for Disinfecting Products based on the Disinfection Efficacy Testing for Products dated May 1, 1997 of the U.S. Food and Drug Administration, Division of Ophthalmic Devices, which requires the solution to pass primary criteria over a minimum recommended disinfection period in that the number of bacteria recovered per mL must be reduced by a mean value of not less than 3.5 logs, and the number of mold and yeast recovered per ml must be reduced by a mean value of not less than 1.5 log within the disinfection period.

2. The method of claim 1, wherein the composition comprises hyaluronic acid at a concentration of 0.005 wt. % to 0.05 wt. %.

3. The method of claim 1, wherein the composition comprises the amphoteric surfactant of general formula I at a concentration of 0.01 wt. % to 0.8 wt. %.

4. The method of claim 1, wherein the lens care solution further comprises 0.5 ppm to 1.3 ppm of poly(hexamethylene biguanide), or 2 ppm to 5 ppm of alexidine.

5. The method of claim 2, wherein the lens care solution further comprises 0.01 wt. % to 0.8 wt. % of the amphoteric surfactant of general formula I.

6. The method of claim 1, wherein the lens care solution further comprises propylene glycol or myristamidopropyl dimethylamine.

7. The method of claim 1, wherein the repeating of steps (a) and (b) occurs at least once every seven days.

* * * * *